United States Patent
Salmisuo et al.

(10) Patent No.: US 8,574,508 B2
(45) Date of Patent: Nov. 5, 2013

(54) METHOD OF COOLING A STERILIZER

(75) Inventors: Mauri Salmisuo, Tuusula (FI); Jani Pettersson, Hyvinkää (FI)

(73) Assignee: STERIS Europe, Inc. Suomen Sivuliike, Tuusula (FI)

( * ) Notice: Subject to any disclaimer, the term of this patent is extended or adjusted under 35 U.S.C. 154(b) by 267 days.

(21) Appl. No.: 13/089,579

(22) Filed: Apr. 19, 2011

(65) Prior Publication Data

US 2011/0274592 A1     Nov. 10, 2011

(30) Foreign Application Priority Data

May 4, 2010 (FI) ...................................... 20105484

(51) Int. Cl.
- *A61L 2/00* (2006.01)
- *A61L 9/00* (2006.01)

(52) U.S. Cl.
USPC ............................................................. 422/292

(58) Field of Classification Search
USPC ............................................................. 422/292
See application file for complete search history.

(56) References Cited

U.S. PATENT DOCUMENTS

| | | | |
|---|---|---|---|
| 3,897,818 A | 8/1975 | Champel | 165/1 |
| 4,497,773 A | 2/1985 | Kuelzow et al. | 422/26 |
| 2003/0145806 A1 | 8/2003 | Tokutake et al. | 122/459 |
| 2005/0112040 A1* | 5/2005 | Hasegawa et al. | 422/300 |

FOREIGN PATENT DOCUMENTS

| | | | |
|---|---|---|---|
| EP | 0297010 | 12/1988 | A23L 3/10 |
| EP | 0387136 | 9/1990 | A61L 2/07 |
| EP | 0788402 | 5/2001 | B01J 3/04 |
| GB | 1502271 | 3/1978 | A23L 3/10 |
| RU | 2051690 | 1/1996 | A61L 2/00 |

OTHER PUBLICATIONS

International Search Report issued in a corresponding European Application No. EP 11 397509) dated Jun. 17, 2011; 2 pages.

* cited by examiner

*Primary Examiner* — Walter D Griffin
*Assistant Examiner* — Christopher Vandeusen
(74) *Attorney, Agent, or Firm* — Kusner & Jaffe; Michael A. Centanni

(57) ABSTRACT

A method for cooling a jacketed autoclave or steam sterilizer by allowing a film of water to flow down as inner wall of the sterilizer's jacket. Condensate from the jacket space is drawn into a water ring pump. The water ring pump draws condensate from the lowest point of the jacket to a water side of the pump, and gas from the jacket to a normal suction inlet of the pump. During the process of cooling the sterilizer, a stream of water and air from the water ring pump is conducted to an upper part of the jacket of the steam sterilizer and is allowed to flow as a film down the inner wall of the jacket. Evaporation of the water is enhanced by lowering the pressure in the jacket.

6 Claims, 1 Drawing Sheet

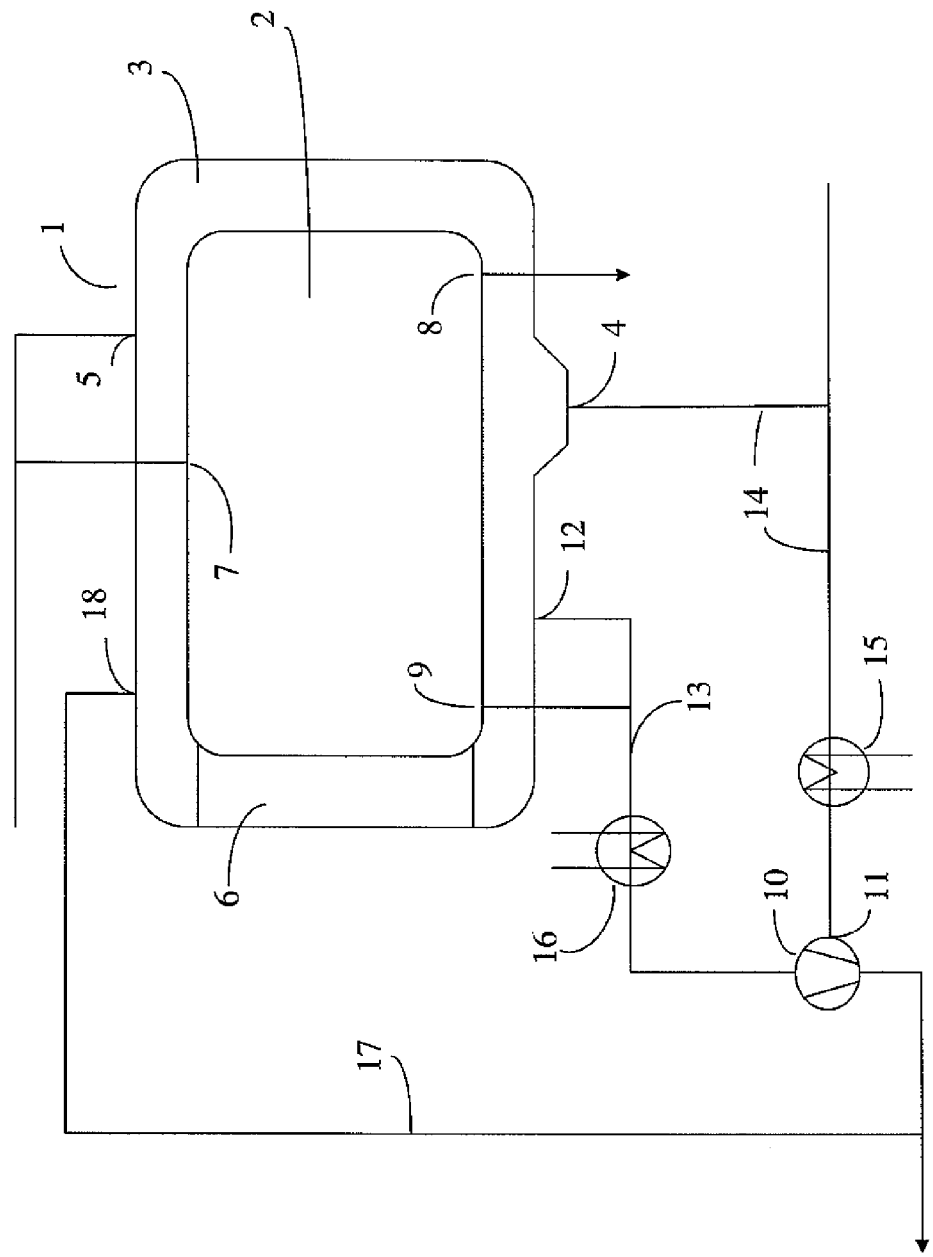

METHOD OF COOLING A STERILIZER

FIELD OF THE INVENTION

The invention relates to the cooling of the load of a steam-operated sterilizer. In particular, the invention relates to the efficient use of condensate for cooling.

BACKGROUND OF THE INVENTION

A steam autoclave for sterilizing purposes consists of a chamber with steam inlets and condensate outlets as well as other necessary connections for vacuum etc. Often a jacket is provided for temperature control, the jacket having connections for steam supply, condensate removal, vacuum and venting. An autoclave or steam sterilizer as described may go through a number of operational phases during use, like charging a load, removing the air, heating up to a temperature, exposing the load to the temperature and sterilization media, cooling and discharging the load, with several cycle variations.

Heating up is carried out with steam acting directly on the load in the chamber. Prior to the heating up stage, air is removed from the chamber by pulling a vacuum in the chamber and replacing it with steam. Several repetitions of this cycle may be carried out. To minimize condensation on the chamber walls, the jacket may be steam heated. Condensate is usually collected at the side(s) of the jacket, normally so that a small amount of condensate is left on the bottom of the chamber.

Cooling is typically carried out by filling the jacket with cold water and allowing a flow until the desired temperature is reached. The water consumption during this stage is significant.

As explained above, a vacuum system is conventionally provided in steam autoclave systems, usually served by a water ring pump. A water ring pump (in this context, the expression "liquid ring pump" is equivalent to "water ring pump") is a device in which a vaned impeller rotates to form a moving cylindrical body of liquid, which forms the seal of a series of compression chambers formed by the space between the vanes. The eccentric placement of the impeller within the pump housing gives rise to a cyclic variation in the volume enclosed by the vanes and the water ring. The ring liquid is partly entrained with the discharge stream, and must be replaced by fresh makeup liquid or with cooled and recycled liquid separated from the discharge stream.

Since a water ring pump can draw gas-liquid mixtures without problems, they are well suited for autoclave service. The vacuum obtainable with a liquid ring pump is dependent on the vapor pressure of the liquid in question at the operating temperature. To maintain the vacuum capacity, the liquid must often be cooled.

SUMMARY OF THE INVENTION

According to the invention, cooling of a jacketed autoclave or steam sterilizer is carried out by allowing a film of water to flow down the inner wall of the jacket space. Connections to the vacuum system are provided in the jacket space at the lowest point for recovering condensate and at a higher point for lowering the pressure in the jacket.

After the exposure stage is completed, condensate from the jacket space is drawn into the water ring pump provided for vacuum in the autoclave jacket. Since the pressure in the water ring is lower than in the jacket, the condensate can be conducted to the water side of the pump, i.e. the condensate connection is to the pump housing, which is internally covered by water during pump operation. The normal suction line is connected at the pump to the gas zone closer to the impeller shaft at the site of maximum compression chamber volume, and the discharge connection is in the gas zone at the site of minimum compression chamber volume. According to the invention, a connection is provided also at a point above the lowest in the jacket space for lowering the jacket pressure.

Thus, the water ring pump draws condensate from the lowest point of the jacket to the water side, and gas from the jacket space to the normal suction inlet. A stream corresponding to the entering condensate must be expelled from the water ring pump to maintain the proper water level in the pump.

According to the invention, during the cooling stage a stream of water and air from the water ring pump is conducted to the upper part of the jacket space of the steam sterilizer and is allowed to flow as a film down the inner wall of the jacket space. Evaporation takes place with cooling of the jacket inner wall. This evaporation is enhanced by the lowering of pressure in the jacket due to the action of the water ring pump. Thus, the autoclave is cooled by a film of water flowing across the jacket inner wall while evaporating.

The filling of the jacket space with cooling water is avoided with considerable savings in terms of water consumption. Furthermore, the volume of water needed in the present cooling stage of the jacketed steam sterilizer is inherently available at the bottom of the jacket, generated as condensate of the pure steam consumed during the previous phases of the cycle. This water reservoir does not need to be replenished with fresh water for accomplishing the described cooling function.

To maintain the required temperature in the water ring pump, cooling of the entering streams is required. Closed-circuit cooling water is commonly available in industrial settings, and consequently none of this cooling water is wasted, either.

BRIEF DESCRIPTION OF THE DRAWING

FIG. 1 is a schematic view of a device according to the invention.

DETAILED DISCLOSURE OF THE INVENTION

The invention will now be described in greater detail with reference to the accompanying drawing. An autoclave 1 having a chamber 2 surrounded by a jacket space 3 is shown in FIG. 1. The load of material for sterilization is charged through hatch 6. A steam inlet to the chamber is provided at 7 and a corresponding condensate outlet at 8, as well as a vacuum connection at 9. Conventionally provided lines for venting, safety valves etc. not significant for the understanding of the invention are not shown. Shut-off and control valves as conventionally provided are also not shown in the piping required for the invention.

In the context of the present invention the term jacket space 3 (or briefly jacket 3) means the space surrounding the chamber 2. The jacket space 3 is typically one space defined by jacket walls as shown in FIG. 1, but also other possible constructions are within the scope of the invention. The jacket space 3 may for example comprise interconnected spaces, separated spaces (tanks) connected to the main jacket. The volume of the jacket space 3 can vary and is optimized case by case.

According to the invention, connecting lines are now provided between the vacuum system and the jacket 3. At 4 is the lowermost point for the collection of condensate from the jacket space 3. During the jacket 3 heating up stage, this condensate results from condensation of steam supplied to the jacket through inlet 5. The line 14 from this point, the condensate line, is connected to liquid ring pump 10 at a connection 11 situated in the region of the liquid ring.

At 12 is a connection situated in the jacket 3 at a point above the connection for condensate withdrawal 4. Line 13 connects this to the normal gas suction inlet of the liquid ring pump 10.

Heat exchangers 15 and 16 are provided in lines 14 and 13, served with cooling water from e.g. a closed plant cooling water system.

A sterilization process begins, after the load has been charged into chamber 2, with the evacuation of air 9 from the chamber 2 and subsequent steam feed 7. The evacuating and steam feeding cycle is repeated as required, and the sterilization process continues until the air is removed, and the required amount of heat has been delivered to the load, i.e. the exposure stage is completed. The amount of heat is dependent on the nature of the load, and the requirements and details of the sterilization process itself are well known to the skilled person.

The following stage involves cooling of the load. According to the invention, condensate or stream of water from the jacket space 3, collecting at connection 4, is drawn to the liquid ring through line 14, and cooled before entering the pump 10 in exchanger 15. Typically some condensate exists in the jacket space, conventionally on the bottom thereof, during the whole sterilization operation. Additionally air is drawn via connection 12 from the jacket space 3, along line 13 to the pump 10, wherein it is mixed with cooled condensate i.e. water entering at connection 11. From the liquid phase of the pump 10, a stream of water and air is conducted to the upper part of the jacket 3 through line 17. Distributor means (not shown) are provided at connection 18 to distribute the mixture of water and air over the inner wall of the jacket space 3. There is typically from 4 to 10 beams in the top of the jacket 3, from which beams the distribution of the mixture of water and air can be operated evenly throughout the whole area (length and width) of the jacket 3. The distribution arrangement can be carried out for example so that the second stream 17 is branched to separate streams, the number of separate streams corresponding to the number of beams in the top of the jacket 3, in a lower point than is the location of the beams, to make sure that the distribution is even throughout the whole area of the jacket 3.

The pressure within the jacket space 3 is lowered, whereby the evaporation of the water flowing as a film over the jacket inner wall is enhanced, increasing the cooling effect.

After completing the cooling stage the load is removed from the autoclave 1 through hatch 6 and a new sterilization operation can be started by charging a new load.

The invention claimed is:

1. A method for cooling a jacketed steam sterilizer, said method comprising the steps of:
    withdrawing a first stream of liquid water from a jacket space at a lowest point in said jacket space wherein the jacket space is not supplied with additional liquid water from an external source during the operation of the cooling function;
    conveying said first stream of liquid water directly to a point within a liquid phase of a liquid ring pump;
    conveying a second stream of liquid water and air from the liquid ring pump to a point within the jacket space to form a liquid water film that flows down an inner wall of the jacket space.

2. A method according to claim 1, wherein said air is withdrawn from the jacket space at point above the lowest point of the jacket space, and said air is conducted to the liquid ring pump wherein the air is mixed with said first stream of liquid water.

3. A method according to claim 2, wherein said air is cooled in a heat exchanger before entering the liquid ring pump.

4. A method as in one of claims 1 to 3, wherein said first stream of liquid water is the only stream of liquid water entering the liquid ring pump.

5. A method as in one of claims 1 to 3, wherein the pressure in the jacket space is lowered during said method.

6. A method as in one of claims 1 to 3, wherein the first stream of liquid water is cooled before entering the liquid ring pump.

* * * * *